United States Patent [19]
Gier

[11] Patent Number: 6,089,226
[45] Date of Patent: Jul. 18, 2000

[54] SELF CONTAINED, CRYOGENIC MIXED GAS SINGLE PHASE STORAGE AND DELIVERY

[75] Inventor: Harold L. Gier, Boulder, Colo.

[73] Assignee: Aerospace Design & Development, Inc., Boulder, Colo.

[21] Appl. No.: 09/008,393

[22] Filed: Jan. 16, 1998

Related U.S. Application Data

[63] Continuation of application No. 08/755,249, Nov. 22, 1996, Pat. No. 5,709,203.

[51] Int. Cl.$^7$ ....................................................... A62B 7/06
[52] U.S. Cl. ............................... 128/201.21; 128/DIG. 27
[58] Field of Search ......................... 128/201.21, 205.22, 128/201.27, DIG. 27

[56] References Cited

U.S. PATENT DOCUMENTS

| | | |
|---|---|---|
| 1,448,590 | 3/1923 | Gensecke . |
| 1,459,158 | 6/1923 | Lisse . |
| 2,460,269 | 2/1949 | Appeldoorn . |
| 2,562,164 | 7/1951 | Hinkson . |
| 2,970,452 | 2/1961 | Beckman et al. ................... 128/201.21 |
| 3,062,017 | 11/1962 | Belcar et al. . |
| 3,064,448 | 11/1962 | Whittington . |
| 3,079,765 | 3/1963 | Le Vantine . |
| 3,085,405 | 4/1963 | Frantti . |
| 3,097,497 | 7/1963 | Fitt .................................... 128/201.21 |
| 3,161,192 | 12/1964 | McCormack . |
| 3,211,216 | 10/1965 | Coleman, Jr. et al. . |
| 3,227,208 | 1/1966 | Potter, Jr. et al. . |
| 3,248,897 | 5/1966 | Stark . |
| 3,279,201 | 10/1966 | Wortz et al. . |
| 3,289,748 | 12/1966 | Jennings . |
| 3,318,307 | 5/1967 | Nicastro . |
| 3,411,156 | 11/1968 | Feher . |
| 3,430,688 | 3/1969 | Crocker . |
| 3,463,150 | 8/1969 | Penfold . |
| 3,487,765 | 1/1970 | Lang . |
| 3,526,223 | 9/1970 | Curtis . |
| 3,570,481 | 3/1971 | Woodberry, Jr. . |
| 3,572,048 | 3/1971 | Murphy . |
| 3,635,216 | 1/1972 | Curtis . |
| 3,699,775 | 10/1972 | Cowans . |
| 3,736,764 | 6/1973 | Chambers et al. . |
| 3,738,367 | 6/1973 | Hardy . |
| 3,743,012 | 7/1973 | Laxo . |
| 3,744,555 | 7/1973 | Fletcher et al. . |
| 3,827,246 | 8/1974 | Moen et al. . |
| 3,869,871 | 3/1975 | Rybalko et al. . |
| 3,875,749 | 4/1975 | Baciu . |
| 4,024,730 | 5/1977 | Bell et al. . |
| 4,095,593 | 6/1978 | Webbon et al. . |
| 4,172,454 | 10/1979 | Warncke et al. . |
| 4,181,126 | 1/1980 | Hendry . |
| 4,211,086 | 7/1980 | Leonard et al. ................... 128/201.21 |

(List continued on next page.)

OTHER PUBLICATIONS

"Supercritical Cryogenic Self–contained Breathing Apparatus", Dr. H.L. Gier, final R & D report, Engineering Report 1025 (whole document), Aug. 13, 1990.

Tzimoulis, Paul J.; "I dived on liquid air"; pp. 22–29; Skin Diver, Jun. 1967.

*Primary Examiner*—John G. Weiss
*Assistant Examiner*—Joseph F. Weiss, Jr.
*Attorney, Agent, or Firm*—Harold A. Burdick

[57] ABSTRACT

A system and method for storage and delivery of a cryogenic mixed gas is disclosed, the storages apparatus including a compact and lightweight dewar for containing cryogenic temperature mixed gas at supercritical pressure. Different heat exchangers associated with the dewar provide for heat input to the dewar to maintain gas therein in a single phase and provide continued expulsion energy. A backpack receives the dewar and includes means for quick connect of the dewar with an end use outlet, intermediate heat exchangers in the backpack conditioning the mixed gas for end use. No electrical input for fluid circulation is required.

15 Claims, 10 Drawing Sheets

U.S. PATENT DOCUMENTS

| | | |
|---|---|---|
| 4,459,822 | 7/1984 | Pasternack . |
| 4,500,432 | 2/1985 | Poole et al. . |
| 4,807,447 | 2/1989 | Macdonald et al. . |
| 4,961,325 | 10/1990 | Halvorson et al. . |
| 4,977,747 | 12/1990 | Frejaville et al. . |
| 4,998,415 | 3/1991 | Larsen . |
| 5,062,424 | 11/1991 | Hooker . |
| 5,092,129 | 3/1992 | Bayes et al. . |
| 5,115,859 | 5/1992 | Roebelen, Jr. et al. . |
| 5,201,365 | 4/1993 | Siegel . |
| 5,214,926 | 6/1993 | Mandin et al. . |
| 5,237,824 | 8/1993 | Pawliszyn . |
| 5,269,293 | 12/1993 | Loser et al. .......................... 128/204.15 |
| 5,315,988 | 5/1994 | Clarke et al. ....................... 128/204.23 |
| 5,499,623 | 3/1996 | Pasternack ......................... 128/201.21 |
| 5,511,542 | 4/1996 | Hall ................................... 128/201.21 |
| 5,577,498 | 11/1996 | Yoshida et al. .................... 128/205.28 |

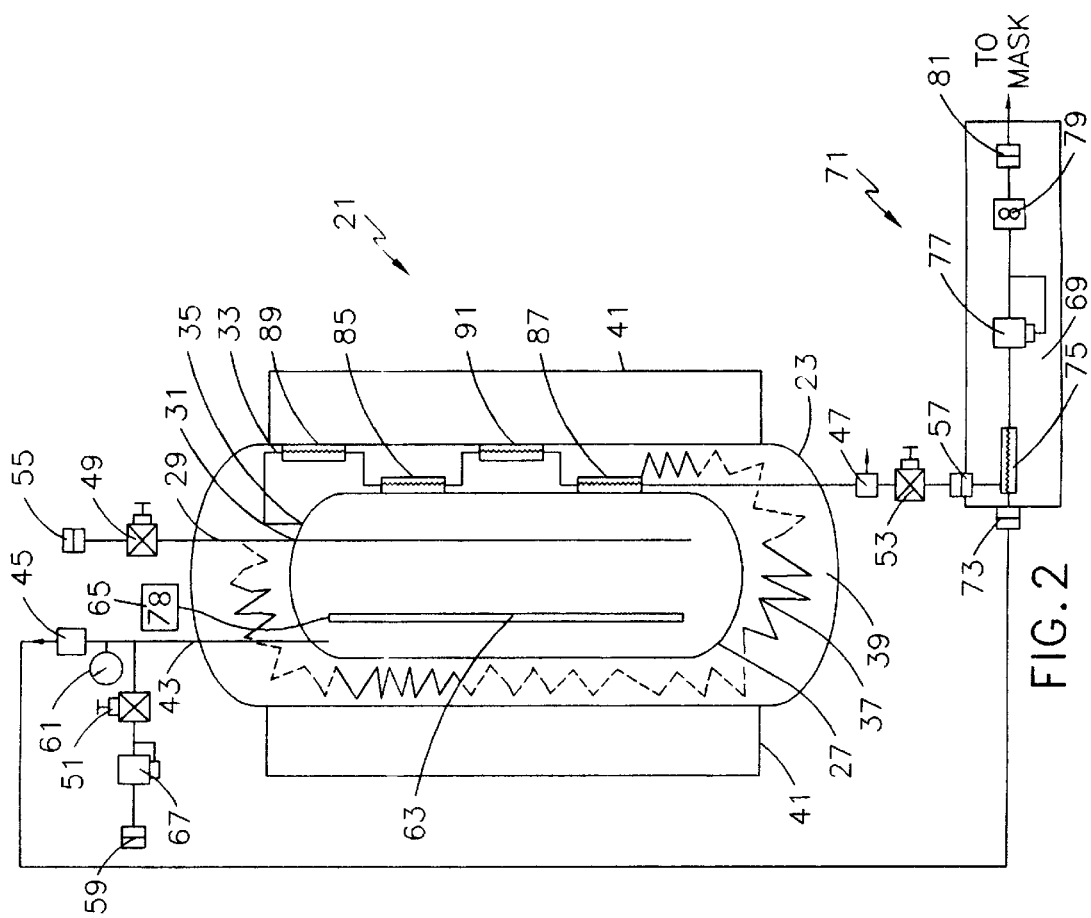
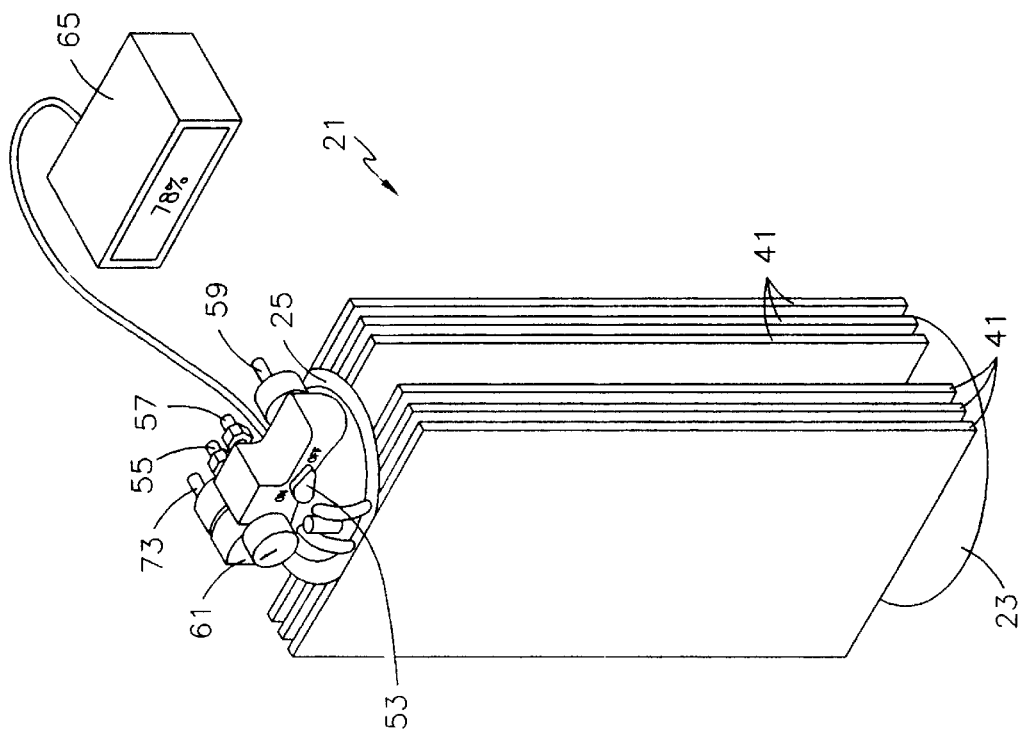
FIG. 2
FIG. 1

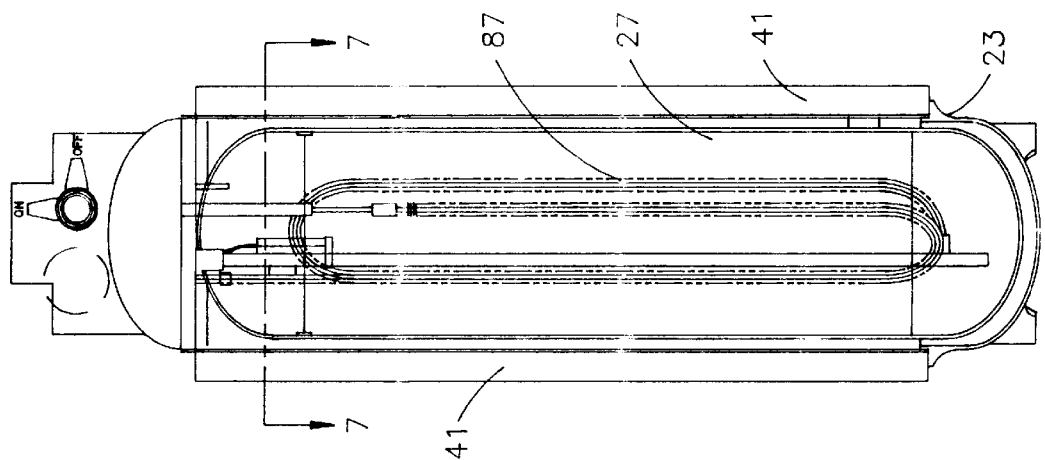
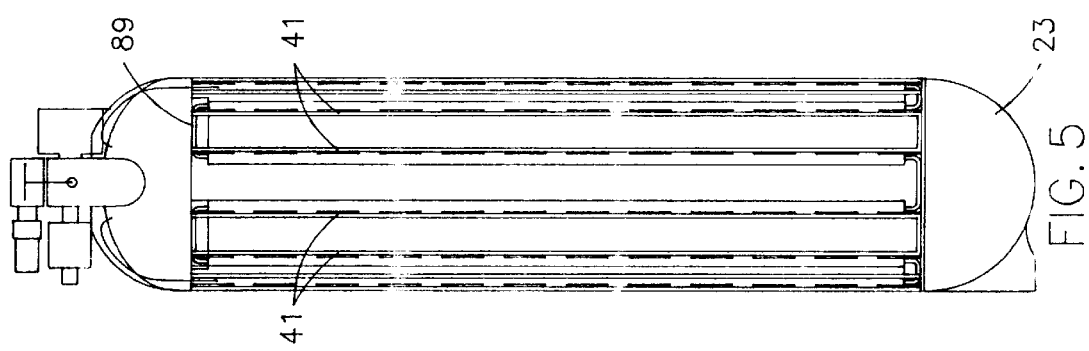
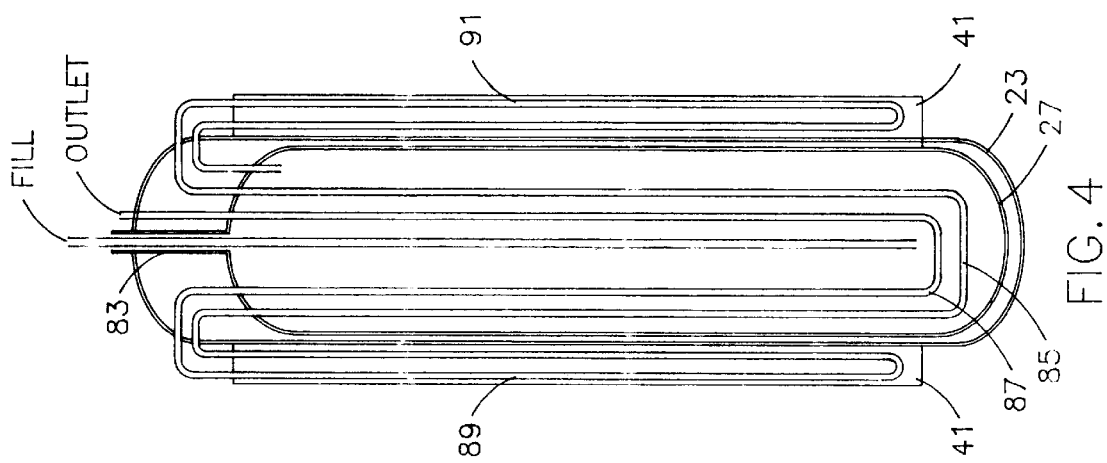

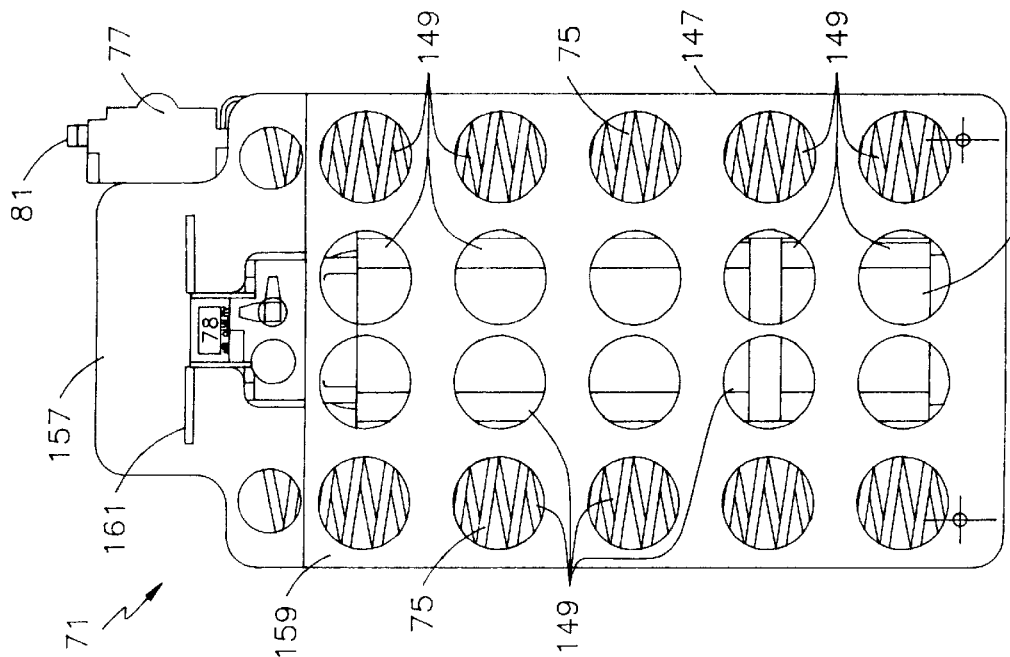
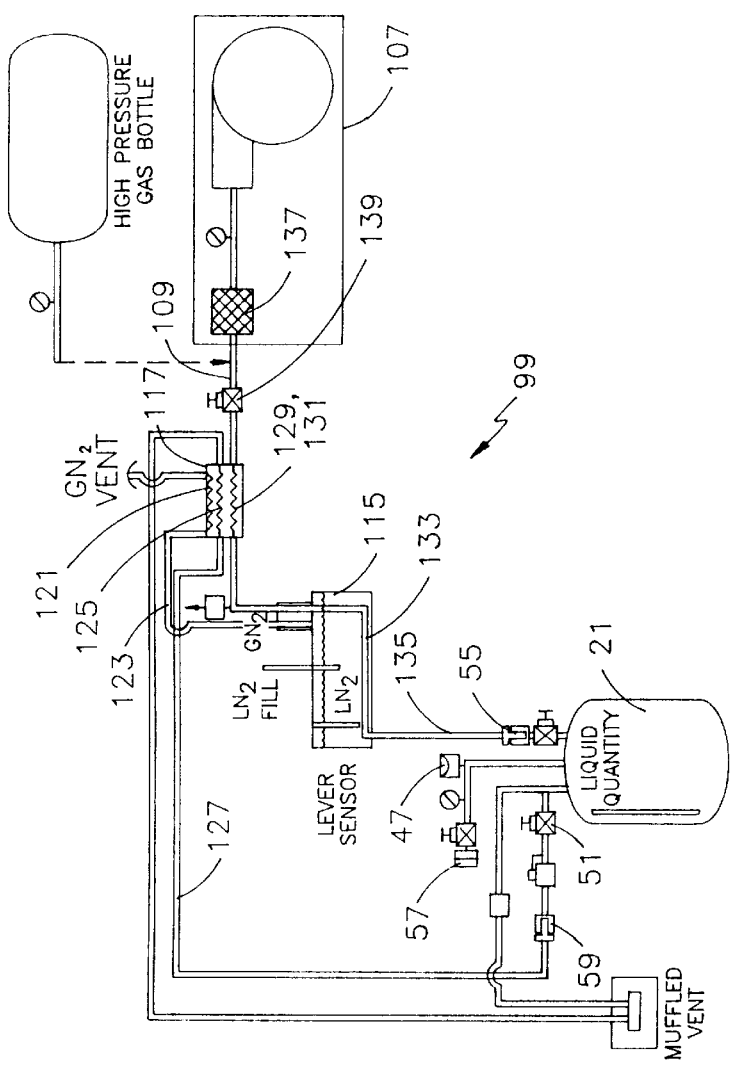
FIG. 12
FIG. 11

SELF CONTAINED, CRYOGENIC MIXED GAS SINGLE PHASE STORAGE AND DELIVERY

RELATED APPLICATION

This Application is a continuation of now pending U.S. patent application Serial No. 08/755,249 filed Nov. 22, 1996 entitled "Self Contained, Cryogenic Mixed Gas Single Phase Storage and Delivery System and Method for Body Cooling, Gas Conditioning and Utilization" by Harold L. Gier (issued as U.S. Pat. No. 5,709,203 on Jan. 20, 1998), which is a continuation of U.S. patent application Ser. No. 08/328,743 filed Oct. 24, 1994 entitled "Heat Exchange in a Mixed Gas Delivery System for Body Cooling and Gas Conditioning" by Harold L. Gier (now abandoned) and a continuation-in-part of U.S. patent application Ser. No. 08/480,555 entitled "Loading, Storage and Delivery Apparatus and Method for Fluid at Cryogenic Temperature" filed Jun. 7, 1995 by Harold L. Gier and Richard L. Jetley (now abandoned), which Applications are a continuation-in-part and a continuation, respectively, of now abandoned U.S. patent application Ser. No. 07/879,581 filed May 7, 1992 and entitled "Loading, Storage and Delivery Apparatus And Method For Fluid At Cryogenic Temperature" by Harold L. Gier and Richard L. Jetley.

GOVERNMENT SUPPORT

This invention was made with Government support under contracts awarded by the National Aeronautics and Space Administration and the U.S. Air Force. The Government has certain rights in the invention.

FIELD OF THE INVENTION

This invention relates to body cooling and fluid storage and delivery apparatus and methods, and, more particularly, relates to integrated systems for body cooling and delivery and conditioning of mixed gas initially contained at cryogenic temperature.

BACKGROUND OF THE INVENTION

High pressure, ambient temperature gas storage and delivery devices have been heretofore suggested for providing attitude independent supply of mixed gasses such as breathable air to a user thereof. Such devices, while in use, have limited gas delivery time, are bulky, and must be operated at extremely high pressures.

Liquid air storage and delivery devices have also been suggested (see U.S. Pat. Nos. 1,448,590, 3,318,307, 3,570,481, 3,572,048, 4,181,126, 3,699,775, 1,459,158, and 3,227,208), but suffer from limited standby time due to oxygen enrichment inherent in such storage, some being unduly complex in an effort to confront this problem, are not attitude independent, and are often quite heavy.

Dispensers for cryogenic temperature elemental and compound gasses (below −175° F.) such as oxygen held for use at supercritical pressure (above 730 psia) have been heretofore suggested (see U.S. Pat. Nos. 3,062,017 and 3,827,246) In such dispensers a heat transfer mechanism (i.e., an electrical heating element or a heat exchanger) is utilized to pressurize the storage vessel having liquid oxygen loaded therein at atmospheric pressure (thus making the dispenser less than desirable as an air supply, where oxygen enrichment could occur while liquid air is in standby storage) for expelling the oxygen.

Pressure sensing is thereafter used to sense the heat transfer needs in the vessel to maintain pressure therein above critical pressure by activating the heating element periodically. Heat exchange is accomplished utilizing at least in part active means separate from the dewar thus encumbering these heretofore known dispensers with complex sensing and activating mechanisms to assure proper heat input. Improvement in such dispensers could thus still be utilized Liquid cooling garments for body cooling using liquid circulating through a network incorporated in the garment have also been heretofore known and/or utilized (see U.S. Pat. Nos. 3,430,688 and 3,289,748). In at least one case, such a garment has been used with a liquid oxygen converting system to provide an integrated cooling and breathing system (see U.S. Pat. No. 4,024,730).

While the integrated system above described may be effective in some applications, such system fails to provided a compact unit (capable of being carried on one's body) such as might be required by fire fighters or other mobile personnel needing such a system. Such systems require electrical input (undesirable in gaseous environments), rely on manual activation to (control flow rates and thus cooling, and make no use of heat exchange to control system operational parameters other than temperature of the breathable air. Moreover, the oxygen converting systems used therein suffer many of the same drawbacks as heretofore discussed. Further improvement could thus be utilized.

SUMMARY OF THE INVENTION

This invention provides a body mountable mixed gas storage and delivery system and method which maintains conditioning of a mixed gas for end use. The system is lightweight and includes a containment apparatus (or vessel) for storing mixed gas received at cryogenic temperature and supercritical pressure and delivering the mixed gas at a non-cryogenic temperature to a utilization fixture, such as a breathing mask in the case of air or a torch or engine in the case of other mixed gasses. The system requires no electrical input, requires no manual manipulation to control cooling fluid flow rates, and makes use of passive heat exchange for control of system operational parameters including temperature of the usable gas and maintenance of remaining stored gas in a single phase and at proper expulsion pressure.

The containment vessel has an outlet for selective expulsion of the mixed gas from the containment vessel to the utilization fixture and a passive heat exchanger thereat for receiving mixed gas expelled through the outlet and routing the mixed gas at the containment vessel to introduce sufficient heat into the containment vessel so that the mixed gas remaining in the containment vessel is in a single phase. Heat exchange is calculated and configured for introducing heat into the containment vessel at a rate determined by the rate of expulsion of the mixed gas from the containment vessel through the outlet to thereby maintain sufficient energy to expel the mixed gas remaining in the containment vessel and so that the mixed gas remaining is in the single phase.

A body mountable unit is provided and includes a pack structure configured for releasably receiving the containment vessel. The unit includes conditioning means integrally maintained in the pack structure and connectable with the passive heat exchanger when the containment vessel is mounted in the pack structure, the conditioning means for raising the temperature of the mixed gas to a usable temperature.

The containment vessel preferably includes a pressure vessel having an inlet and outlet and an outer shell having the pressure vessel therein. Surface area increasing means, such as fins, are connected with the outer shell for effectively increasing surface area of the outer shell, the mass flow heat exchanger connected adjacent to the outer shell and with the outlet of the pressure vessel for receiving the mixed gas from the pressure vessel through the outlet and conducting it to a connection.

The body mountable unit preferably includes a quick disconnect connected with the conditioning means and readily connectable/disconnectable with the connection of the heat exchanger when the containment vessel is mounted in the pack structure.

The method for storing and delivering mixed gas of this invention includes the steps of loading cryogenic temperature mixed gas into a container so that the mixed gas at time of use is in a single phase, with the container configured to be mountable in a pack that can be carried on the body of a user. Mixed gas is selectively expelled from the container and routed to deliver sufficient heat to the container so that mixed gas remaining in the container remains in the single phase. The expelled mixed gas is received, conditioned for end use, and delivered at structure integrally associated with the pack.

It is therefore an object of this invention to provide an improved self contained cryogenic mixed gas single phase storage and delivery system and method.

It is another object of this invention to provide an improved integrated body mountable mixed gas storage, conditioning and delivery system and method.

It is still another object of this invention to provide a lightweight apparatus for storing mixed gas received at cryogenic temperature and supercritical pressure and delivering the mixed gas at a non-cryogenic temperature to a utilization fixture, such as a breathing mask in the case of air or a torch or engine in the case of other mixed gasses.

It is still another object of this invention to provide a cryogenic mixed gas storage and delivery apparatus which makes use of heat exchange for control of apparatus operational parameters including temperature of the usable gas and maintenance of remaining stored gas in a single phase and at proper expulsion pressure.

It is another object of this invention to provide a body mountable system for mixed gas storage and delivery comprising containment means for receiving mixed gas at cryogenic temperature and in an amount so that the mixed gas is initially at a pressure sufficient to maintain the mixed gas in a single phase, outlet means connected with the containment means for selective expulsion of the mixed gas from the containment means therethrough, passive heat exchange means connected with the outlet means for receiving the expelled mixed gas at the outlet means and conducting the expelled mixed gas to a connection, the heat exchange means being routed for introducing heat into the containment means at a rate determined by a rate of expulsion of the mixed gas from the containment means through the outlet means to thereby maintain sufficient energy to expel the mixed gas remaining in the containment means from the containment means and so that the mixed gas remaining in the containment means remains in the single phase, and a body mountable unit including a pack structure configured for releasably receiving the containment means, the outlet means and the passive heat exchange means therein, the unit including conditioning means integrally maintained in the pack structure and connectable with the connection of the passive heat exchange means when the containment means, the outlet means and the passive heat exchange means are mounted in the pack structure, the conditioning means for raising the temperature of the mixed gas to a usable temperature.

It is another object of this invention to provide an air storage and delivery system comprising an air storage and maintenance unit including a pressure vessel for containing air at cryogenic temperature and at a pressure so that air in the vessel is in a single phase, the vessel having an inlet and an outlet, an outer shell having the pressure vessel therein, surface area increasing means connected with the outer shell for effectively increasing surface area of the outer shell, and mass flow heat exchange means connected adjacent to the outer shell and with the outlet of the pressure vessel for receiving the air from the pressure vessel through the outlet and conducting the air to a connection, the heat exchange means being routed for introducing heat by free convection into the air being conducted to the connection and into the pressure vessel from the air thus routed to thereby maintain sufficient energy in the pressure vessel to expel the air therefrom, and a body mountable pack structure configured for releasably receiving the air storage and maintenance unit therein, the pack structure including a quick disconnect connected with conditioning means integrally maintained in the pack structure and readily connectable/disconnectable with the connection of the heat exchange means of the unit when the unit is mounted in the pack structure, the conditioning means for assuring the air is of a breathable temperature.

It is still another object of this invention to provide a method for storing and delivering mixed gas comprising the steps of loading cryogenic temperature mixed gas into a container so that the mixed gas at time of use is in a single phase, configuring the container to be mountable in a pack to be carried on the body of a user, selectively expelling the mixed gas from the container, routing the expelled mixed gas to deliver sufficient heat to the container so that mixed gas remaining in the container remains in the single phase, and receiving, conditioning for end use, and delivering the expelled mixed gas at structure integrally associated with the pack.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a perspective view of the fluid storage and delivery apparatus used in this invention;

FIG. 2 is a schematic diagram of the apparatus of FIG. 1;

FIG. 4 is a diagrammatic sectional illustration of the storage and delivery apparatus of FIG. 1;

FIG. 5 is a side view of the outer routed portion of the heat exchanger of the storage and delivery apparatus of FIG. 1;

FIG. 6 is a sectional view illustrating part of the inner routed portion of the heat exchanger of the storage and delivery apparatus of FIG. 1;

FIG. 11 is a diagram illustrating operation of the loading apparatus of FIG. 9;

FIG. 12 is a rear view of a carriage and conditioning unit used with the apparatus of FIG. 1;

DESCRIPTION OF THE INVENTION

Figure 3:
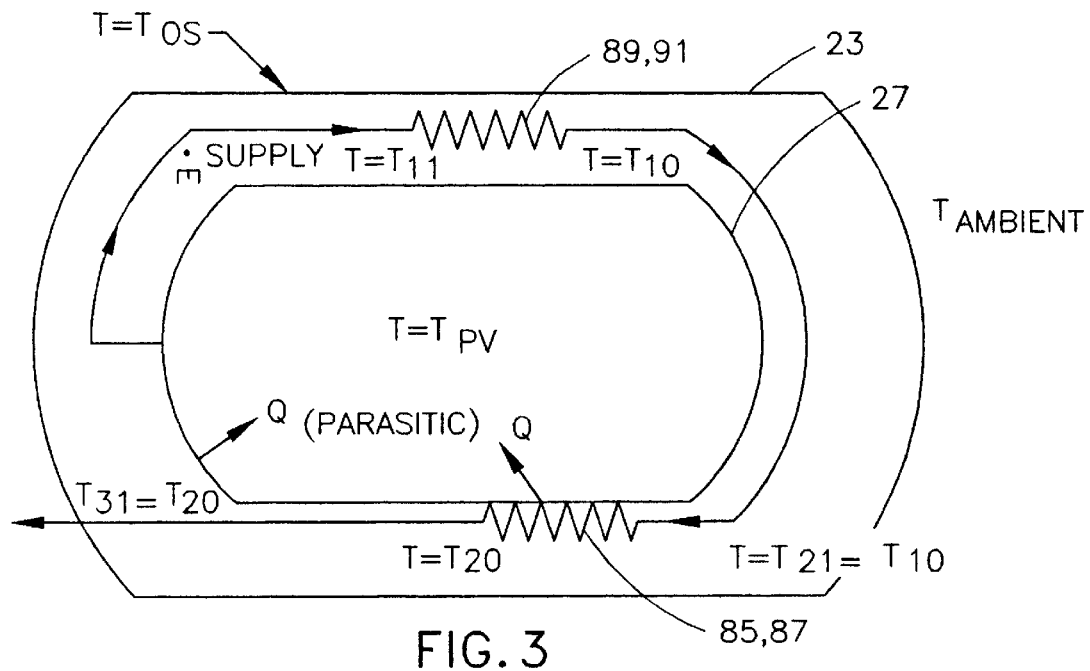
FIG. 3 is a diagrammatic illustration of heat exchange in the apparatus of FIG. 1.

Storage and delivery apparatus 21 (incorporated into, or used in association with, this invention) is shown in FIG. 1 for containing supercritical pressure cryogenic air as a breathing supply to thus obviate the problems of oxygen enrichment and attitude dependence of a liquid air breathing bottle. The use of a supercritical cryogenic fluid state for the air provides a gas which is in a single phase, high density condition and which can be withdrawn from any location in the apparatus which may itself be in any attitude. Supercritical pressure is required so that the air at cryogenic temperature will exhibit no two phase characteristics.

While an air delivery apparatus will be described and referred to herein, it should be understood that the apparatus could as well be used for any fluid, delivery to a utilization fixture, for example elemental and/or compound gasses, or, most particularly, mixed gasses such as air (nitrogen-oxygen), helium-oxygen, argon-oxygen, helium-argon, methane-hydrogen, or the like where prevention of separation of the components due to gravitational effects and/or due to frictional separation from boiling of a liquid is desired.

The critical pressure for air is 37.25 atm. (547.37 psia) and the critical temperature is 132.5 K (238.54° R). The colder the initial temperature of the air (preferably down to 140° R) and to a much lesser extent the higher the pressure (preferably in a range between 750 psia and 2,000 psia), the greater will be the storage density and thus the ability to provide significant rated use times while utilizing smaller, lighter storage units.

The use of supercritical fluid also provides a standby storage advantage over liquid in that energy required to expel a pound of fluid in the single phase storage condition is greater than that required to boil-off a pound of liquid and expel the vapor (161.68 Btu/Lbm at 750 psia versus 86.67 Btu/Lbm at one atmosphere, respectively). Supercritical air may thus be stored for longer times before reservicing than liquid air.

As shown in FIGS. 1 and/or 2, apparatus 21 includes outer shell, or vacuum jacket, 23, protective head 25 (for example, a one-piece cast aluminum head) sealed to shell 23 and pressure vessel 27 within shell 23 for containing the air. Fill line 29 passes through shell 23 and vessel 27 at inlet 31 for filling and/or refilling as hereinafter set forth (all connections and passages with, to and from vessel 27 and shell 23 set forth herein being formed by means known to those skilled in the pertinent art). Passive heat exchange and fluid transport system 33 is connected to vessel 27 at outlet 35 for conducting air expelled from vessel 27 to a use destination (for example to the carriage and conditioning unit hereinafter described).

Insulation 37 fills, and is vacuum jacketed within, space 39 between vessel 27 and shell 23 and can be, for example, formed of ten layers of multi-layered insulation consisting of double aluminized MYLAR spaced with tissue glass (a borosilicate fiber paper) or polyester netting. Fins 41 (in one embodiment being about four inches wide by 0.083 inch thick aluminum fins) are welded to, or formed integrally with (though they could also be remote from the shell), shell 23 for effectively increasing the surface area of the shell exposed to ambient temperature air to enhance heat exchange as discussed in more detail hereinbelow.

Vent line 43 is connected with vessel 27 for relief venting through relief valve 45 and to maintain pressure during standby and during filling. Relief valve 45 should include a TEFLON seal and be rated for cryogenic temperatures, and as illustrated is preferably biased at atmospheric pressure for relieving top pressure and thus reducing pressure through transport system 33 without waste of fluid. Relief valve 47 is employed as a final high reliability safety device, and should be sized to relieve at approximately 10% (approximately 200 psi) above relief pressure of valve 45.

Flow control valves 49, 51 and 53 are manual valves for control of filling, draining and use of apparatus 21, and may be bellows type valves of all welded construction designed for temperature cycling application;, and/or may be combined into one or more operational units. Quick disconnects 55, 57, and 59 are provided for making required connections to a loading apparatus for example, as hereinafter described) or carriage and conditioning unit.

Pressure gauge 61, for example a small bourdon tube pressure gauge, is used for checking tank pressure, and quantity sensor 63 having readout 65 monitors fluid quantity in vessel 27 (for example, using a capacitance probe to measure the dielectric constant which varies from approximately 1.4 in the full condition to 1.0 in the empty condition). An audible alarm can be provided to alert a user when the fluid quantity reaches a selected low level, all electronics being powered, for example, by a 9 volt battery.

Pressure regulator 67 is a back-pressures regulator used, in conjunction with valve 51, to maintain pressure during standby and filling operations. As shown in FIG. 2, line 43 may be couplable through valve 45 with conditioning unit 69 at carriage and conditioning unit 71 using quick disconnect 73 so that air expelled therethrough may be used in the system.

Conditioning unit 69 includes heat exchanger 75 for heating expelled air to a breathable temperature, pressure regulator 77, optional flowmeter 79 and quick disconnect 81 for connection with a utilization device such as a mask.

Configuration of the various components varies with operation. During storage, valves 49 and 53 and quick disconnects 55, 57 and 81 are all closed. During loading operations valves 49 and 51, quick disconnects 55 and 59 and pressure regulator 67 are operational. During standby, valve 51, quick disconnect 59 and pressure regulator 67 remain open, while in operation valve 51, quick disconnect 59 and pressure regulator 67 are closed, and valve 53 is opened.

Vessel 27, in one particularly useful embodiment, has a volume of less than 4.2 liters (preferably about 4 liters), the apparatus having an overall diameter of about five inches, length of about 22 inches, operating pressure of 1,600 psia, and weight empty of about 10.7 pounds (filled weight of about 19 pounds) for a rated delivery time of about one hour ("rated delivery" herein refers to NIOSH rating of 40 SLM (standard liters per minute) for breathing apparatus, equating to about 6.7 lbs. of air per hour of delivery). In such case, vessel 27 is made of titanium, though other materials could be used.

By way of further example, for a rated time of two hours at the same operating pressure, the apparatus having a titanium vessel 27 weighs under 30 pounds filled, has a vessel volume of about 7.2 liters, a diameter of 6.5 inches and a length of about 25 inches.

Apparatus weight depends on vessel 27 volume, operating pressure and materials. Pressure vessel and outer shell materials could include composites such as FIBERGLASS, KEVLAR or graphite. Metals that could be used include stainless steel, aluminum, INCONEL or titanium. Aluminum or composite pressure vessels would require bimetal joints, with a composite vessel 27 possibly including an aluminum liner and neck plug 83 (shown in FIG. 4 For housing inlet and outlet plumbing and for, in part, positioning vessel 27 in shell 23) overlaid with an S-glass/epoxy composite (a composite fabric heretofore used in aerospace applications). The advantage in weight of such construction is significant, with a 4 liter apparatus (rated use exceeding 60 minutes) having a diameter of 4.5 inches and a vessel weight of less than four pounds. Overall, weights for a 4 liter apparatus range from about 10.7 to 16.4 pounds at an operating pressure of 1,600 psig, the lightest having a titanium, INCONEL 718 or aluminum (6061-T6 welded and heat treated with a burst pressure in excess of 6,000 psig) vessel 27 with an aluminum shell 23.

Figure 7:
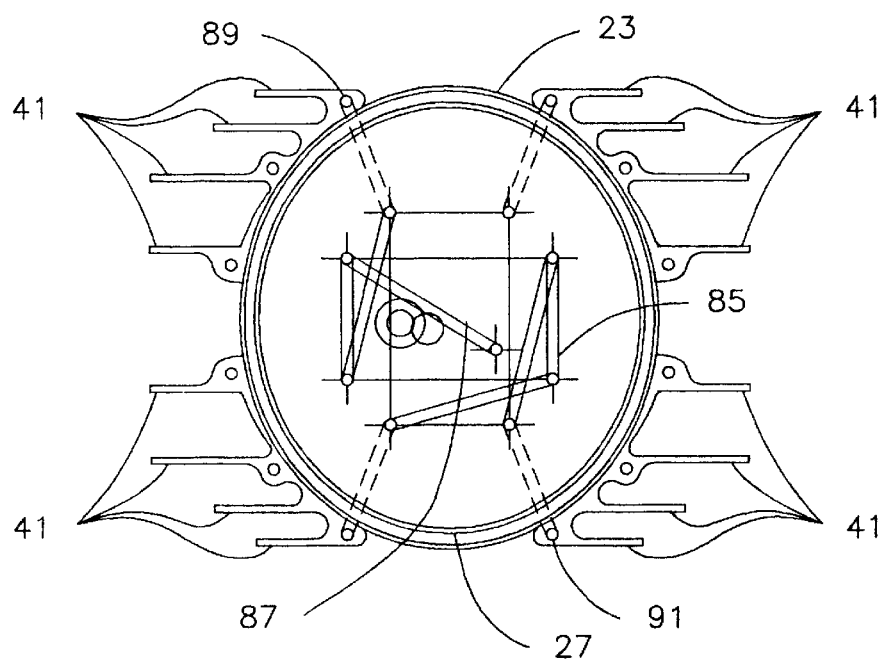
FIG. 7 is a sectional view taken through section line 7—7 of FIG. 6.

Referring now to FIGS. 2 and 3, passive heat exchange system 33 is a double loop heat exchange system (a single loop system could be used in a system as hereinafter set forth) including inner exchange loop portions 85 and 87 connected either to the outer part of vessel 27 or passing into vessel 27 in direct contact with fluid therein. Outer exchange loop portions 89 and 91 are connected with shell 23 or fins 41 or could be made integral to fins 41 as shown in FIG. 7. The heat exchange loop portions are preferably constructed of ⅛" diameter aluminum tubing, though other materials could be utilized.

Sufficient heat must be efficiently transported from outer shell 23 to pressure vessel 27 to maintain the gas in the vessel in the single phase and to provide expulsion energy for delivery of the gas from the vessel. A design to provide adequate heat transfer for expulsion must recognize that the process is a transient one. Fluid conditions and properties constantly change throughout the entire expulsion process.

For example, the expulsion energy for supercritical air ranges from approximately 35 BTU/Lbm to 160 BTU/Lbm in the pressure and temperature range of interest, with the integrated average expulsion energy being approximately 65 BTU/Lbm. Since heat leak through plumbing and other fixtures alone is insignificant compared to that required to expel the air needed (only about 9.0 BTU/Hr for a shell temperature of 530° R and a vessel temperature of 180° R) for use by an individual user at maximum exertion (estimated to be about 16.0 lbm/hr), mass flow heat exchange system 33 must be calculated to deliver sufficient heat for operation of the apparatus.

An example demonstrating heat transfer requirement for a single point in the expulsion process follows. As illustrated by FIG. 3, expelled tank fluid passes through heat exchangers 89/91 increasing its temperature to nearly that of the surface of outer shell 23 (preferably by free convection to the ambient air though various means of forced convection of ambient air to shell 23 could be utilized to provide more energy exchange). The fluid then flows to heat exchangers 85/87, respectively, cooling the fluid and dumping heat for fluid expulsion and single phase maintenance into fluid remaining in pressure vessel 27. The maximum amount of heat (Q) that can be transported from shell 23 to vessel 27 depends on the mass flow rate of outflowing fluid ($m_{supply}$), the specific heat of the cryogenic air ($C_p$), and the temperature difference between shell 23 and vessel 27 as in the following equation:

$$Q = m_{supply} C_p (T_s - T_v)$$

Since the $C_p$ of cryogenic air varies with temperature, a more accurate representation of the heat transported is:

$$Q = m_{supply}(h_s - h_v)$$

where $h_s$ is the enthalpy of air at the outer shell temperature and fluid pressure and $h_v$ is the enthalpy of air at the pressure vessel temperature and fluid pressure.

A realistic number for heat exchanger efficiency is considered to be 0.90, so that the Q calculated above would be multiplied by this efficiency twice (for external and internal heat exchangers) to obtain a heat flux for the heat exchanger described. Assuming a nominal fluid pressure of 800 psia, an ambient temperature of 530° R ($h_s$=122 BTU/Lbm) and pressure vessel fluid temperature of 150° R ($h_v$=-48 BTU/Lbm), the total Q transferred to the pressure vessel fluid is $$Q = (0.9)(0.9)16.0 Lbm/Hr(122-(-48))BTU/Lbm \quad Q = 2200 BTU/Hr$$

Taking these numbers into consideration as well as the required increase in temperature of vessel 27, a double loop exchange system as shown would be required to achieve approximately 2480 Btu/hr that will drive 16 lbm/hr out of vessel 27 while remaining single phase.

In order to predict the amount of heat transfer between the outer shell and ambient air, a free convection correlation for a long horizontal cylinder geometry is utilized so that heat transfer by free convection, $q_{conv}$, from ambient air to shell 23 is given by:

$$q_{conv} = h\pi DL(T_S - T_\infty)$$

where h equals the average free convection film coefficient, D equals cylinder diameter, L equals cylinder length, $T_S$ equals cylinder temperature, and $T_\infty$ equals ambient air temperature. The free convection film coefficient may be obtained from the dimensionless Rayleigh number, Ra, by:

$$Ra = g\beta(T_S - T_\infty)L^3/\alpha v$$

where g equals acceleration of gravity, β equals the volume coefficient of expansion, α equals thermal diffusivity, and v equals dynamic viscosity.

In the case at hand, solution for Ra yields $1.4 \times 10^9$. An appropriate correlation for the Nusselt number, Nu, is:

$$Nu_D = 0.10(Ra)^{1/3}$$

which for this example is equal to approximately 110.0. The film coefficient is related to the Nusselt number by:

$$h = (Nu \, k)/L$$

where the thermal conductivity, k, for air at the average air temperature is 0.013 BTU/Hr-Ft-° F. This results in an average film coefficient, h, of 0.95 BTU/Hr-Ft$^2$-° F.

Thus, for an outer shell area of approximately 2.5 ft$^2$, an ambient temperature of 530° R and average shell temperature of 300° R, the total amount of heat available from free convection will be 550 BTU/Hr. Therefore, a higher product of film coefficient and outer shell 23 surface area is required in order to transfer adequate heat to vessel 27 to maintain desired pressure. Since the free convection heat transfer coefficient is fixed due to geometry and fluid conditions, the only method to increase this product in the embodiment of apparatus 21 shown in FIG. 1 is to effectively increase the surface area of shell 23 as is done utilizing fins 41.

Figure 8:
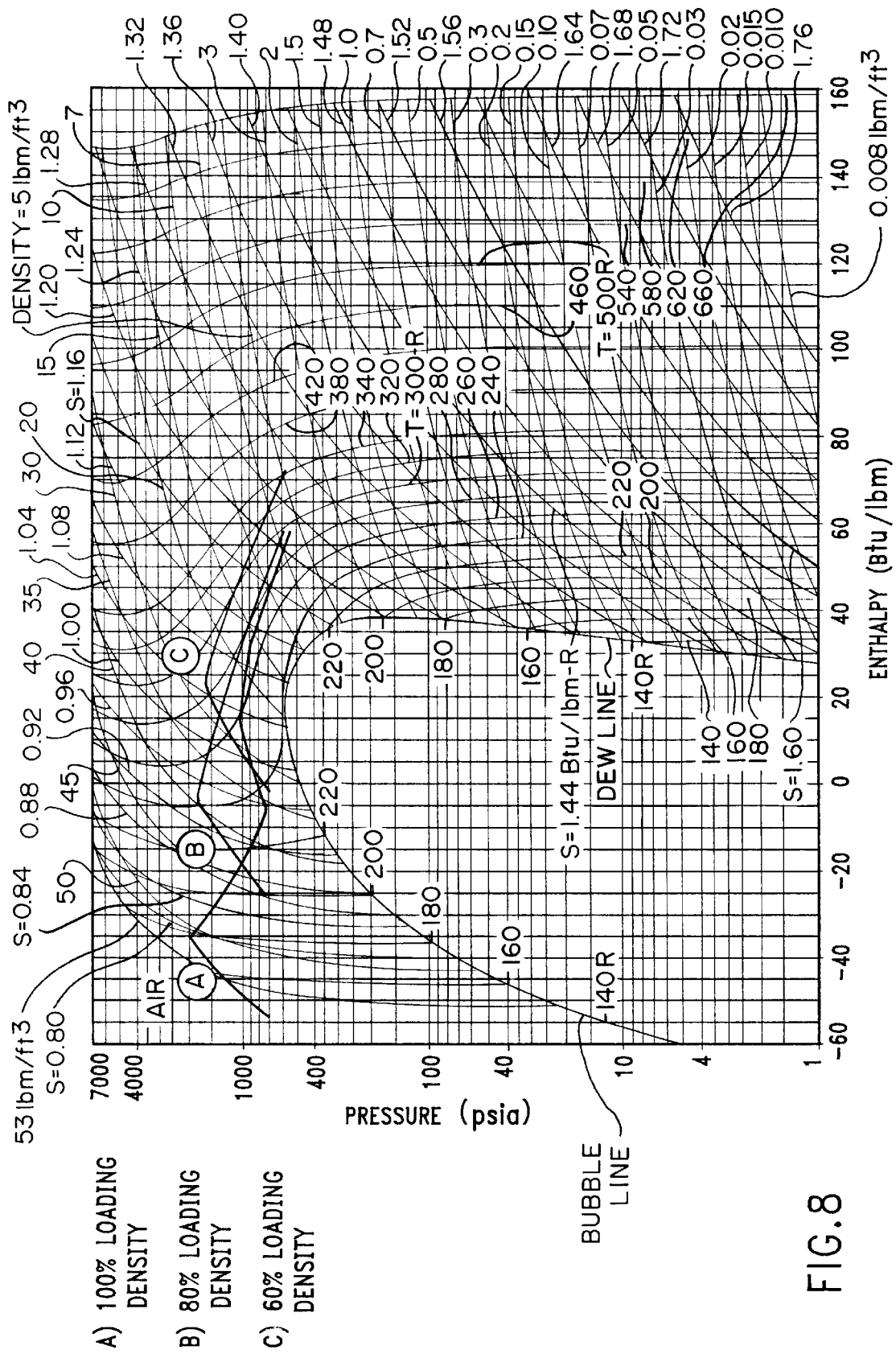
FIG. 8 is a Mollier chart showing performance of the apparatus of FIG. 1 under a variety of loading densities.

FIGS. 4 through 7 show routing of the heat exchange loop portions as suggested hereinabove. For a 3 liter tank design, 63–64 feet total of tubing is utilized for heat exchange system 33. FIG. 8 is a Mollier chart having plotted thereon results of various tests illustrating an adequate degree of separation of the transient fluid condition from the two-phase region utilizing the apparatus of this invention.

While not illustrated herein, vessel 27 is preferably supported in shell 23 on neck tube support 83 attached to both vessel 27 and shell 23. Bumpers, or pads, would be desirable adjacent to the lower, unsupported, end of vessel 27 to thwart movement of vessel 27 in excess of maximum allowable stress to neck 83 or its connections to vessel 27 and shell 23.

Figure 10:
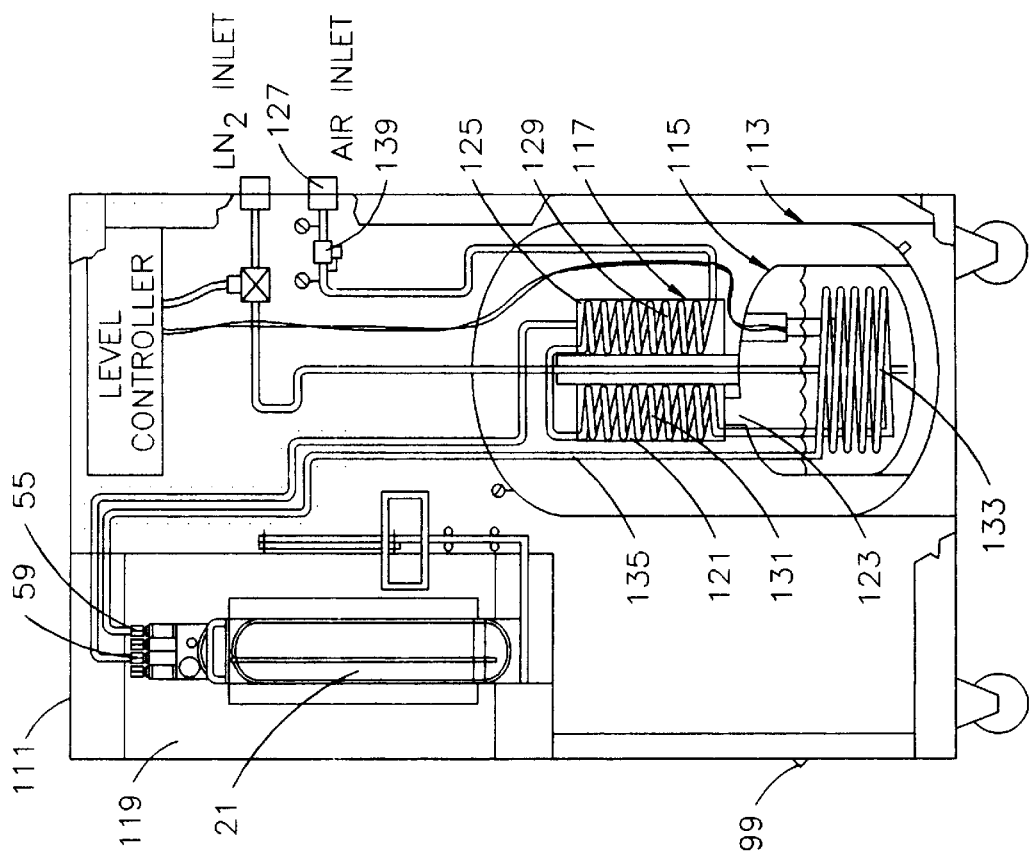
FIG. 10 is a schematic sectional view of the loading apparatus of FIG. 9.
Figure 9:
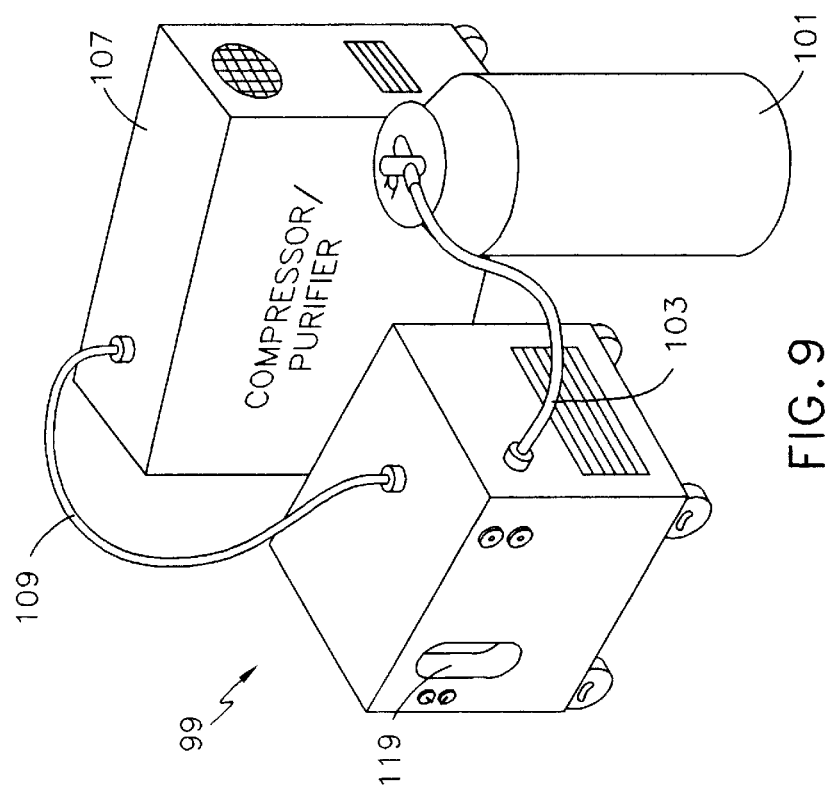
FIG. 9 is a perspective view of a loading apparatus for loading fluid into the storage apparatus.

FIGS. 9 through 11 illustrate a loading apparatus 99 usable with this invention, advantageous in that loading at supercritical pressure is made possible (it being understood that any loading method for placing the cryogenic gas in vessel 27 could be utilized with the body cooling system of this invention as hereinafter set forth). Apparatus 99 has coolant (such as LN$_2$, i.e., liquid nitrogen) supply 101 connected thereto by supply conduit 103 (an LN$_2$ refrigerator or other means could be utilized). Air supply 107 is connected to apparatus 99 by conduit 109 (a compressor being illustrated, though a high pressure compressed air bottle could also be utilized). An alternative fill apparatus could be provided which utilizes a source of cryogenic temperature air itself maintained at supercritical pressure, in which case, loading would be simplified even if possibly more expensive and unwieldy.

Apparatus 99 includes housing 111, vacuum chamber 113 having LN$_2$ bath chamber 115 and precooling chamber 117 therein, and storage apparatus insertion chamber 119 for receipt thereinto of a storage apparatus to be serviced (preferably having a self aligning load, securing and quick disconnect mechanism for ease of use by an operator). Precooling chamber 117 includes heat exchange chamber 121 connected with boil-off line 123 and chamber 125 connected with fill vent quick disconnect 59 from apparatus 21 to provide preliminary cooling (from about 20° C. to about –60° C.) of air received through inlet 127 from supply 107.

Exchange coils 129 and 131 are positioned in chambers 125 and 121, respectively, air flowing in the coils then being passed through LN$_2$ bath in coil 133 of conduit 135 (it should be recognized that mechanical refrigeration could also be utilized) to lower temperature of the air to about –195° C. The air is then received in apparatus 21 through quick disconnect 55. Since the air from supply 107 is received at loading apparatus 99 at or above the critical pressure (about 800 psi), the fluid is received at apparatus 21 in the single phase condition, thus rendering apparatus 21 usable substantially immediately after filling.

Where supply compressor unit 107 is utilized rather than a high pressure gas bottle containing high purity air, filter/dryer/CO$_2$ scrubber 137 and pressure regulator 139 are provided. Compressor supply unit 107 may include for example, an oil-free 1,000 psi compressor. Various gauges, readouts, program controls and the like could be utilized to enhance ease of operation and safety of the apparatus.

Figure 13:
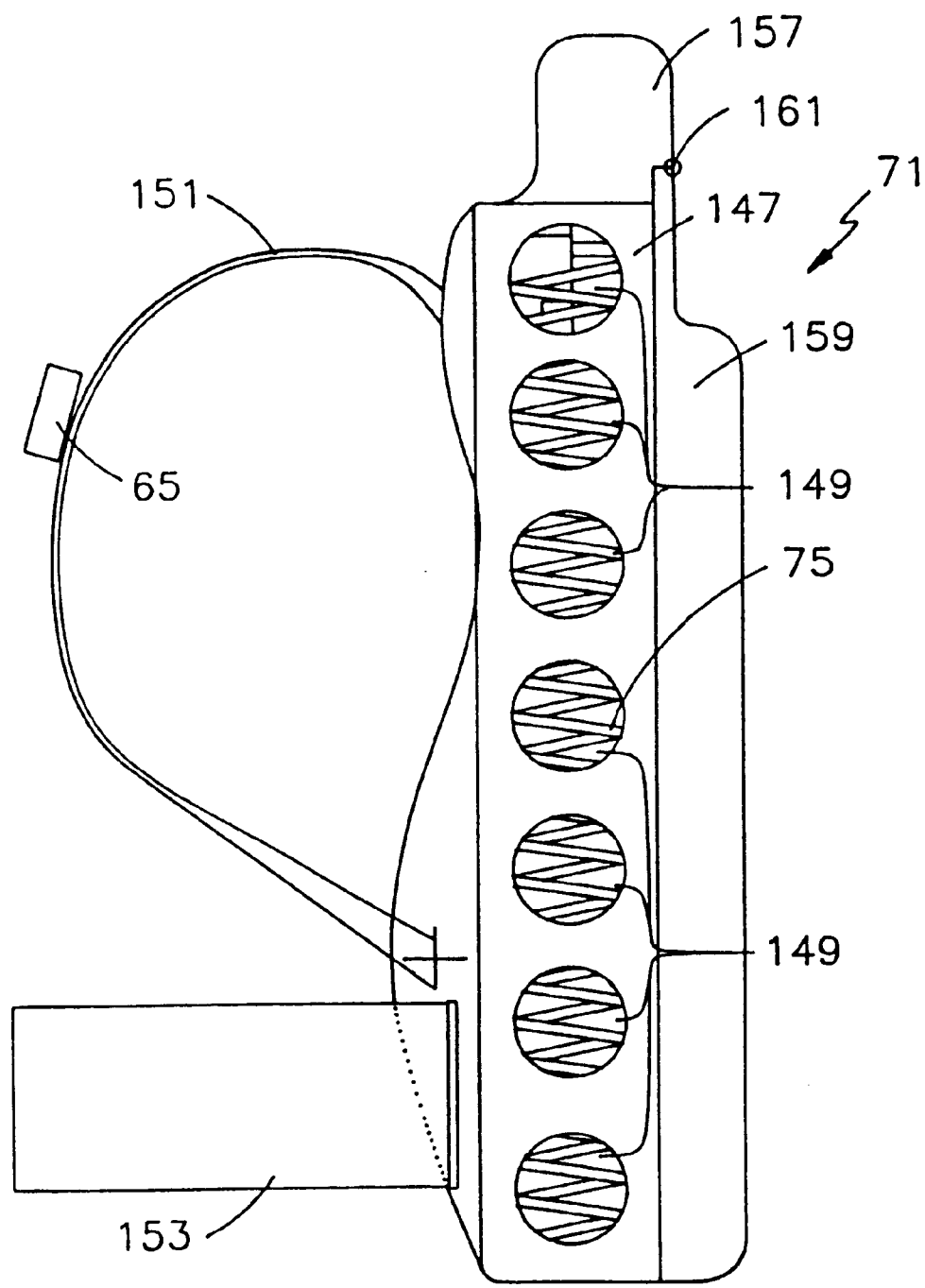
FIG. 13 is a side view of the unit of FIG. 12.

FIGS. 12 and 13 illustrate carriage and conditioning unit 71 utilizable with this invention. Unit 71 includes pack structure 147 made, for example, of high strength light weight molded plastic. Structure 147 has a plurality of openings 149 therein to assure proper flow of ambient air around apparatus 21 and the various heat exchangers mounted therein (for example heat exchanger 75, though the openings will serve the same function for other exchangers as hereinafter set forth). Air conditioning heat exchangers 75 and pressure regulator 77 are mounted on structure 147 by any convenient means, and adjustable harness 151 and waist belt 153 are mounted in selected sets of receiving slots at the back of the pack structure. Remote fluid quantity readout 65 may be attached to harness 151 for ease of observation. Apparatus 21 is snugly maintained in structure 147 by molded head 157 and hinged door 159 connected at hinge 161.

Figure 14:
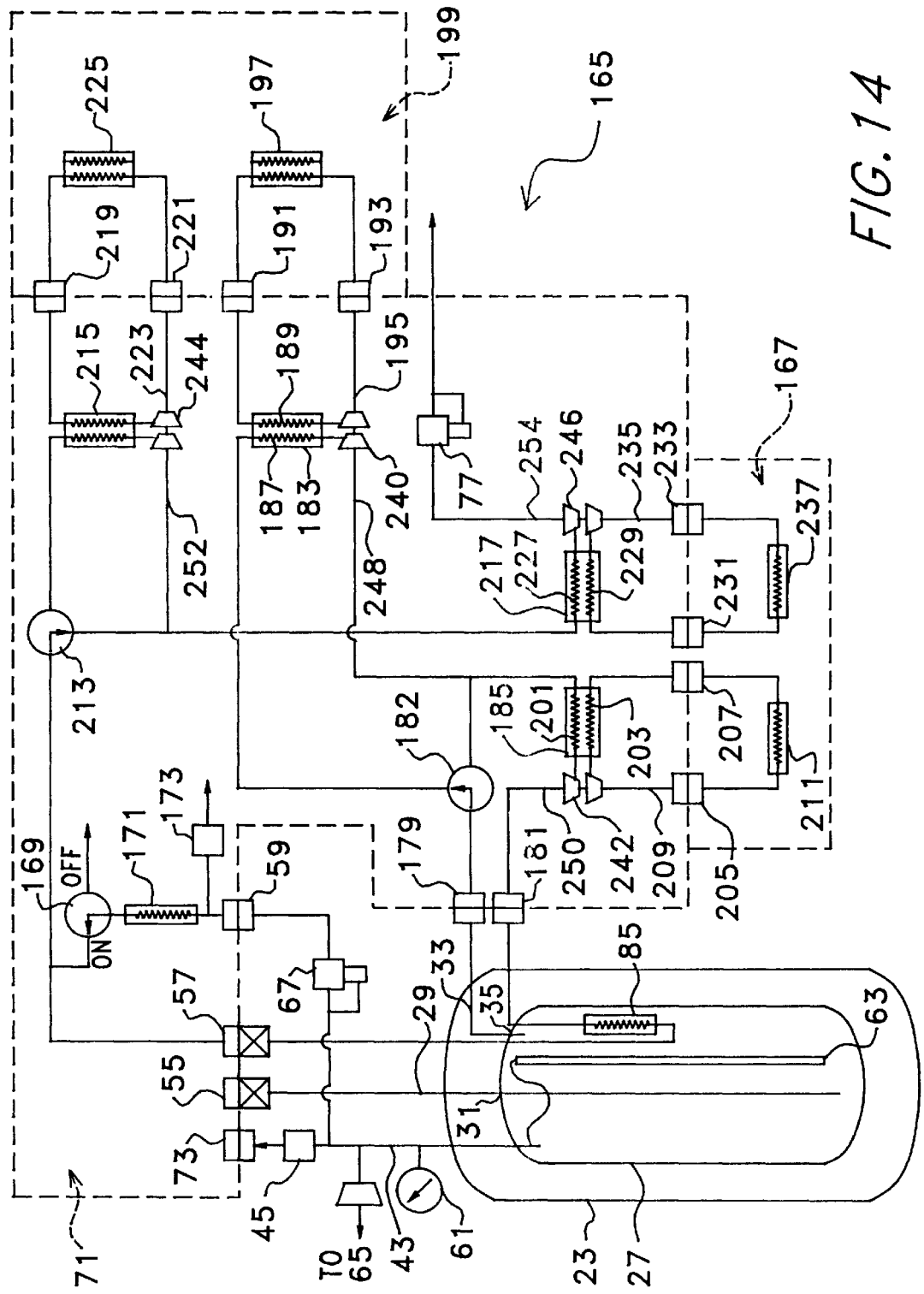
FIG. 14 is a schematic illustration of the body cooling system of this invention used in association with a modified apparatus of FIG. 2.
Figure 15:
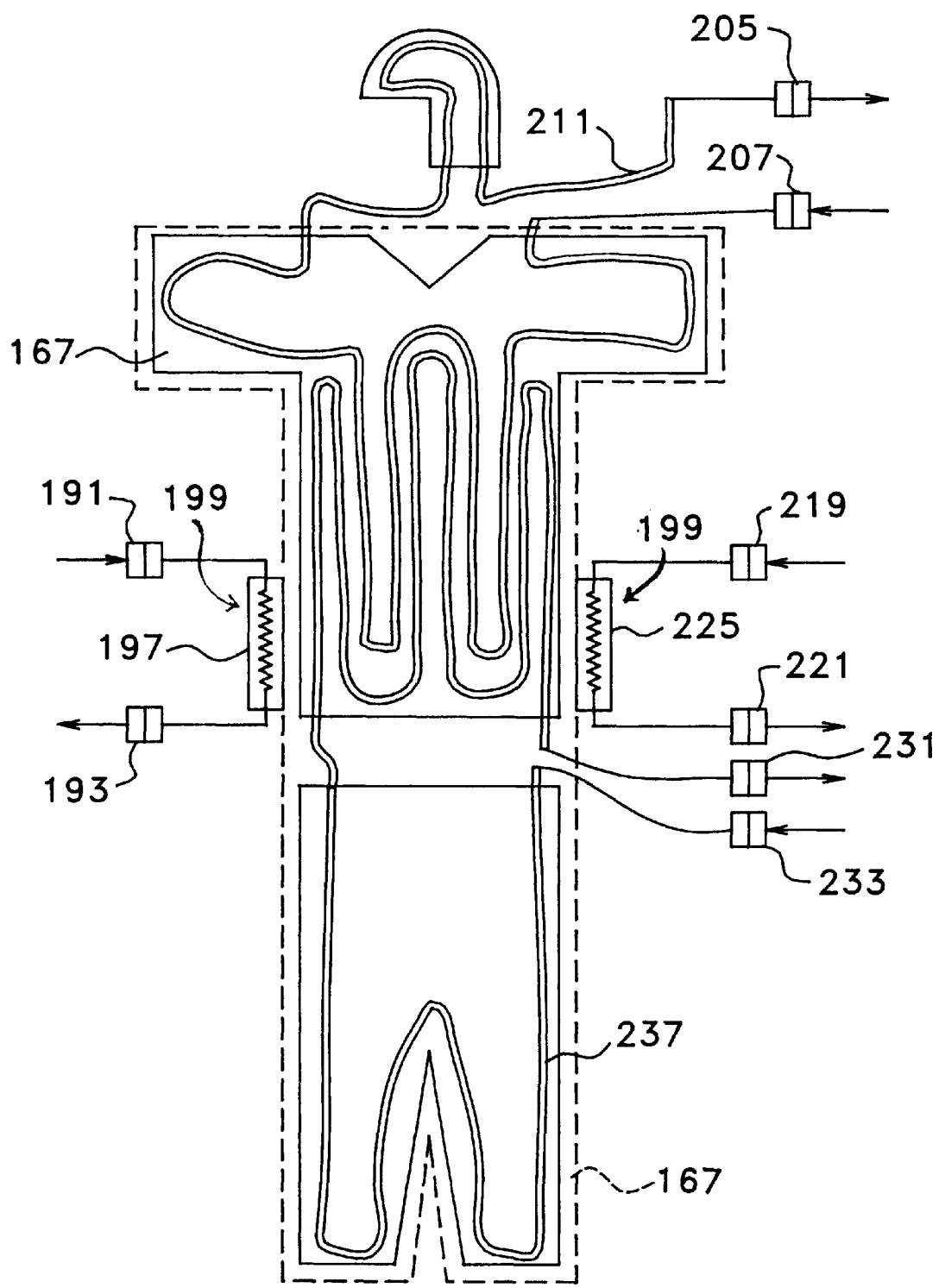
FIG. 15 is a schematic illustration of a fluid circulation network incorporated into a garment for use in the system of FIG. 14.

Turning now to FIGS. 14 and 15 illustrating a first embodiment of body cooling system 165 of this invention, many of the features of apparatus 21 as shown in FIG. 2 remain substantially the same for use with the system, including outer shell 23 having an insulated pressure vessel 27 therein, various outlets 31 and 35, lines 29, 33 and 43, quick disconnects 55, 57, 59 and 73, relief valve 45, pressure regulators 67 and 77, and pressure and quantity gauges and readout 61, 63 and 65. However, only one internal heat exchange loop 85 is required for maintaining cryogenic gas in vessel 27 in a single phase and providing sufficient expulsion pressure since heat input is no longer provided by exchange with the ambient atmosphere (formerly at exchange loops 89 and 91 at fins 41 and shell 23 in FIG. 2), but by heat exchange with fluid heated by the body of a wearer of garment 167.

Quick disconnect 59 is now connected at carriage unit 71 to valve 169 through passive heat exchanger 171 for recycling of gas expelled thereat into the system when valve 169 is on. Valve 169 is off when the unit is not connected at carriage unit 71 and in a standby condition. Relief valve 173 is provided to maintain desired pressure (for relief at about 1,000 psi). Heat exchanger 171 is situated to pre-warm gas before passage through valve 169 to prevent valve damage and thus leaking.

Quick disconnects 179 and 181 are provided for interconnection of vessel 27 at carriage unit 71 with system 165. Mixed gas expelled at outlet 35 through line 33 first reaches control valve 182 where the gas is directed either to pre-warming heat exchanger 183 or directly to body cooling heat exchanger 185, depending on valve setting. Pre-warming heat exchanger 183 includes gas conduit 187 in heat exchange relationship with fluid conduit 189. Fluid conduit 189 is connected by disconnects 191 and 193 into a discrete fluid (water or water and antifreeze) circulation loop 195 including heat exchanger 197 located in an outer protective garment 199 worn over garment 167 for heat exchange with the ambient atmosphere. Gas at conduit 187 is thus warmed (for air, from approximately –160° C. to about –30° to 15 C) before it reaches heat exchanger 185, pre-warming being necessary in some circumstances to prevent over cooling of the user's body.

Body cooling heat exchange and heat exchange for heat input to vessel 27 at heat exchange loop 85 is accomplished at exchanger 185 including gas conduit 201 in heat exchange relationship with fluid conduit 203. Fluid conduit 203 is connected by disconnects 205 and 207 into a discrete fluid circulation loop 209 including heat exchange network (a fluid circulation network in garment 167 as also shown in FIG. 15).

Where pre-warming is not required under the circumstances, valve 182 directs the mixed gas to heat exchanger 185 (in the case of air, at a temperature of about −160° C.) for heat exchange with fluid in loop 209, preferably lowering fluid temperature to no lower than about 10° C., for example, in the case of water or water and antifreeze, and raising the temperature of the gas, for example to about 20° C. in the case of air where fluid circulating in loop 209 is raised in temperature by the user's body at exchange network 211 to about 30° C. Where the gas has been pre-warmed, since gas entering exchanger 185 is of a higher temperature, the overall body cooling effect is controlled (i.e., fluid temperature at network 211 is controlled). The warmed gas is then directed to heat exchange loop 85 through disconnect 181 providing energy as heretofore discussed at vessel 27.

Gas exiting exchange loop 85, again cooled to about −160° C. in the case of air, is presented through quick disconnect 57 at control valve 213 where the gas is directed either to pre-warming heat exchanger 215 or directly to body cooling heat exchanger 217, depending on valve setting. Pre-warming heat exchanger 215 serves the same purpose for exchanger 217 as heretofore described for exchangers 183 and 185, and is similarly arranged for heat exchange, utilizing quick disconnects 219 and 221 to provide fluid circulation loop 223 having external heat exchanger 225.

Body cooling heat exchange and heat exchange to condition gas for use (formerly provided at heat exchanger 75 in FIG. 2), for example to raise the temperature of cryogenic air to a breathable temperature, are accomplished at heat exchanger 217 including gas conduit 227 in heat exchange relationship with fluid conduit 229. Fluid conduit 229 is connected by disconnects 231 and 233 into a discrete fluid circulation loop 235 including heat exchange network 237 a fluid circulation network in garment 167.

Where pre-warming is not required under the circumstances, valve 213 directs the mixed gas to heat exchanger 217 (in the case of air at a temperature of about −160° C.) for heat exchange with fluid in loop 235, preferably lowering fluid temperature to no lower than about 10° C., for example, in the case of water or water and antifreeze, and raising the temperature of the gas, for example to about 20° C. in the case of air where fluid circulating in loop 235 is raised in temperature by the user's body at exchange network 237 to about 30° C. Where the gas has been pre-warmed, since gas entering exchanger 227 is of a higher temperature, the overall body cooling effect is controlled (i.e., fluid temperature at network 237 is controlled). The warmed gas is then directed through valve 77 to a utilization fixture (such as a face mask for breathable air).

While fluid circulation at loops 195, 209, 223 and 235 may be accomplished by any means adequate to the task, non-electrical pumping is preferred. Pumps 240, 242, 244 and 246 are preferably, particularly where the fluid is liquid such as water or water and antifreeze, pneumatic pumps connected into gas outflow lines 248, 250, 252 and 254 from heat exchangers 183, 185, 215 and 217, and into fluid circulation loops 195, 209, 223 and 235. The pneumatic pumps utilize the pressure drop of gas moving thereacross to circulate the fluid in their respective loops.

While again not required, the pumps are preferably variable rate pumps capable of increasing fluid flow rates in the fluid circulating loops responsive to the rate of use of gas through the system and thus moving through the pumps. For example, in the case of air, increased respiratory rate of a user (indicative of work exerted by the user's body) will increase fluid flow rate through networks 211 and 237 and exchangers 185 and 217 thus increasing the rate of cooling of the body precisely at the time that the user demands increased cooling due to an increased work rate.

The pumps are preferably centrifugal or turbine pneumatic pumps capable of operation at gas pressures up to about 1250 psi and providing variable liquid flow rates between about 0.05 and 1 cubic feet per hour at pressures up to about 20 psi. Materials used in construction may be mostly aluminum and nylon, and, though designed to withstand normally cold ambient temperatures, because of placement at the outflow lines form the heat exchangers need not be designed for cryogenic temperatures.

Valves 182 and 213 are preferably automatically controlled by a processor for switching responsive to sensed body temperature and/or air temperature inputs to the processor. Garment 167 as illustrated in FIG. 15 may be either a one or two piece garment of types heretofore known. Heat exchangers 183, 185, 215 and 217, when used with a liquid secondary loop, are designed to provide heat exchange without freezing the liquid in the presence of low flow rates (of the cold gas between about 0.05 and 0.25 cubic feet per hour, and of the liquid between about 0.2 to 1.0 cubic feet per hour).

Figure 16:
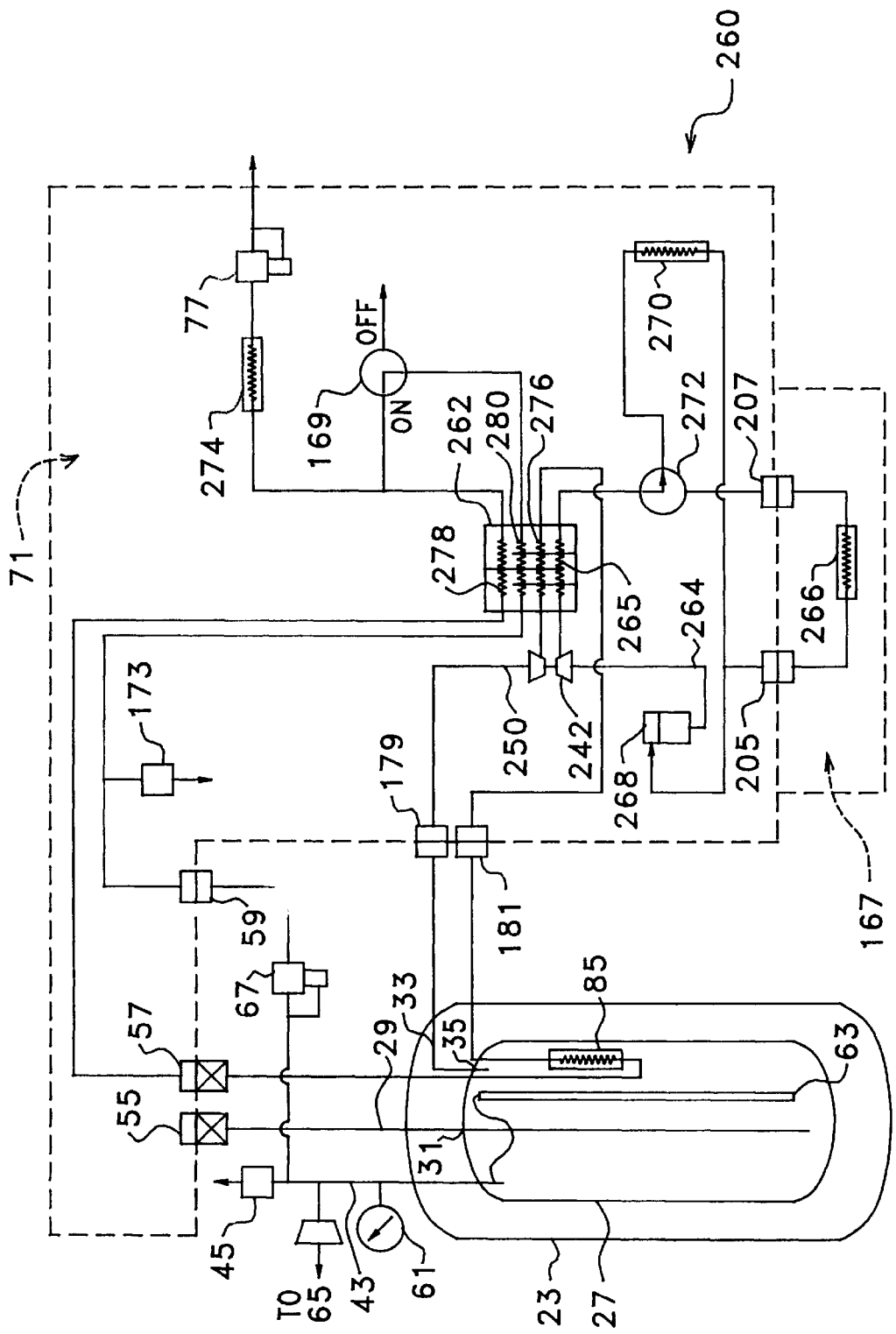
FIG. 16 is a second embodiment of the body cooling system of this invention.

A second embodiment 260 of the body cooling system of this invention is illustrated in FIG. 16. The system illustrated is the same in most regards to that heretofore shown (like elements being indicated by like numbers). However, heat exchanger 262 now combines all heat exchange functions of exchangers 171, 185 and 217 shown in FIG. 14 into a single heat exchange unit. A single fluid circulation loop 264 in circulation with fluid heat exchange conduit 265 of exchanger 262, and including a unified circulation network 266 at garment 167, is provided with fluid supply reservoir 268 at carriage unit 71. Pre-warming heat exchanger 270 (performing the control function of heat exchangers 183 and 215 as shown in FIG. 14) is also located at the carriage structure and is integral with fluid circulation loop 264. Automatic control valve 272 (processor controlled as heretofore discussed with regard to valves 182 and 213) is located in loop 264 for control of fluid flow within the loop. Additional backup heat exchanger 274 is provided to insure adequate conditioning of the mixed gas before use as may be necessary, for example, as a safety feature in a breathing system.

Exchanger 262 includes gas conduits 276 278 and 280, conduits 276 and 278 connected in flow paths and for the functions as heretofore described for conduits 201 and 227 of exchangers 185 and 217 in FIG. 14. Gas conduit 280 is connected in a flow path and for the function as hereto described for exchanger 171 in FIG. 14.

As may be appreciated from the foregoing an improved integrated system and method for body cooling and mixed gas conditioning are provided for use with cryogenic fluid containment and delivery apparatus.

What is claimed is:

1. A body mountable system for mixed gas storage and delivery comprising:

containment means for containing mixed gas received at cryogenic temperature and in an amount so that the mixed gas is initially at a pressure sufficient to maintain the mixed gas in a single phase, said containment means having a volume of 4.2 liters or less for each 60 minute supply of mixed gas deliverable by the system;

outlet means connected with said containment means for selective expulsion of the mixed gas from said containment means therethrough;

passive heat exchange means connected with said outlet means to receive the expelled mixed gas at said outlet means and conduct the expelled mixed gas to a connection, said heat exchange means being routed for introducing heat into said containment means at a rate determined by a rate of expulsion of the mixed gas from said containment means through said outlet means to thereby maintain sufficient energy to expel the mixed gas remaining in said containment means from said containment means and so that the mixed gas remaining in said containment means remains in the single phase; and a body mountable unit including a pack structure configured for releasably receiving said containment means, said outlet means and said passive heat exchange means therein, said unit including conditioning means for conditioning the mixed gas by raising temperature of the mixed gas to a usable temperature, said conditioning means integrally maintained in said pack structure and connectable with said connection of said passive heat exchange means when said containment means, said outlet means and said passive heat exchange means are mounted in said pack structure.

2. The system of claim 1 wherein said pack structure includes positioning structure for assuring proper positioning of said containment means when mounted therein, said body mountable unit further including quick disconnect means for ready connectability/disconnectability of said connection of said passive heat exchange means and said conditioning means of said unit when said containment means, said outlet means and said passive heat exchange means are mounted in said pack structure.

3. The system of claim 1 wherein said mixed gas is air and wherein said containment means is made of materials so that said containment means having air therein sufficient for a breathable air delivery time of about 60 minutes weighs less than about 20 pounds.

4. The system of claim 1 wherein said system further comprises an outer shell having said containment means therein, said heat exchange means being engaged at said outer shell at one portion and adjacent to said containment means at another portion.

5. The system of claim 1 wherein said pack structure of said body mountable unit includes a plurality of openings therein to assure ambient air circulation within said pack structure.

6. The system of claim 1 further comprising relief means biased to ambient pressure for relieving excessive pressure in said containment means while directing mixed gas expelled by the excessive pressure to said conditioning means of said body mountable unit.

7. A body mountable system for mixed gas storage and delivery comprising:

containment means for containing mixed gas received at cryogenic temperature and in an amount so that the mixed gas is initially at a pressure sufficient to maintain the mixed gas in a single phase;

outlet means connected with said containment means for selective expulsion of the mixed gas from said containment means therethrough;

passive heat exchange means connected with said outlet means to receive the expelled mixed gas at said outlet means and conduct the expelled mixed gas to a connection, said heat exchange means being routed for introducing heat into said containment means at a rate determined by a rate of expulsion of the mixed gas from said containment means through said outlet means to thereby maintain sufficient energy to expel the mixed gas remaining in said containment means from said containment means and so that the mixed gas remaining in said containment means remains in the single phase; and a body mountable unit including a pack structure configured for releasably receiving said containment means, said outlet means and said passive heat exchange means therein, said unit including conditioning means for conditioning the mixed gas by raising temperature of the mixed gas to a usable temperature, said conditioning means integrally maintained in said pack structure and connectable with said connection of said passive heat exchange means when said containment means, said outlet means and said passive heat exchange means are mounted in said pack structure, said pack structure of said body mountable unit including a plurality of openings therein to assure ambient air circulation within said pack structure.

8. The system of claim 7 wherein said containment means includes an outer shell having fins connected thereto, said fins having a first portion of said passive heat exchange means incorporated thereinto.

9. The system of claim 8 wherein said containment means includes a pressure vessel within said outer shell, a second portion of said passive heat exchange means being either attached to said pressure vessel or introduced into said pressure vessel.

10. The system of claim 7 wherein said body mountable unit includes positioning structure for assuring proper positioning of said containment means when mounted in said pack structure.

11. The system of claim 7 wherein said passive heat exchange means is routed to deliver sufficient heat to said containment means so that an overall expulsion energy of between about 35 and 160 BTU/Lbm is maintained in said containment means during withdrawal of the mixed gas therefrom.

12. A method for storing and delivering mixed gas comprising the steps of:

loading cryogenic temperature mixed gas into a container so that substantially immediately after the time of loading said mixed gas is at supercritical pressure in said container and at time of use is in a single phase;

configuring said container to be mountable in a pack to be carried on the body of a user;

selectively expelling said mixed gas from said container;

routing said expelled mixed gas to deliver sufficient heat to said container so that mixed gas remaining in said container remains in said single phase; and receiving, conditioning for end use, and delivering said expelled mixed gas at structure integrally associated with said pack.

13. The method of claim 12 wherein the step of routing expelled mixed gas includes the steps of routing said expelled mixed gas to an outer shell containing said container and routing said expelled mixed gas thereafter to said container.

14. The method of claim 12 wherein the step of routing said expelled mixed gas is calculated to deliver sufficient heat to said pressure vessel so that a sufficient overall expulsion energy given thermodynamic characteristics of said mixed gas is maintained in said pressure vessel.

15. The method of claim 12 wherein the step of routing said expelled mixed gas is substantially sufficient to maintain expulsion pressure in said container without need for heat input by an active heat source.

* * * * *